United States Patent
Schlegl et al.

(10) Patent No.: US 11,629,339 B2
(45) Date of Patent: *Apr. 18, 2023

(54) ASEPTIC PURIFICATION PROCESS FOR VIRUSES

(71) Applicant: Valneva SE, Nantes (FR)

(72) Inventors: Robert Schlegl, Siegenfeld (AT); Michael Weber, Vienna (AT)

(73) Assignee: Valneva SE, Nantes (FR)

( * ) Notice: Subject to any disclaimer, the term of this patent is extended or adjusted under 35 U.S.C. 154(b) by 260 days.

This patent is subject to a terminal disclaimer.

(21) Appl. No.: 16/815,215

(22) Filed: Mar. 11, 2020

(65) Prior Publication Data

US 2020/0347364 A1  Nov. 5, 2020

Related U.S. Application Data

(63) Continuation of application No. 15/561,094, filed as application No. PCT/EP2016/057324 on Apr. 4, 2016, now Pat. No. 10,662,412.

(30) Foreign Application Priority Data

Apr. 3, 2015 (EP) .................................... 15248012

(51) Int. Cl.
*C12N 7/00* (2006.01)
*A61K 39/165* (2006.01)
*A61K 39/00* (2006.01)

(52) U.S. Cl.
CPC .............. *C12N 7/00* (2013.01); *A61K 39/165* (2013.01); *A61K 2039/5254* (2013.01); *C12N 2760/18421* (2013.01); *C12N 2760/18434* (2013.01); *C12N 2760/18451* (2013.01)

(58) Field of Classification Search
None
See application file for complete search history.

(56) References Cited

U.S. PATENT DOCUMENTS

| 9,381,238 B2 | 7/2016 | Terrier et al. |
| 10,662,412 B2 | 5/2020 | Schlegl et al. |
| 2018/0119110 A1 | 5/2018 | Schlegl et al. |

FOREIGN PATENT DOCUMENTS

| CN | 102406933 A | 4/2012 |
| EP | 3277802 B1 | 6/2019 |
| WO | WO 2014/031480 A1 | 2/2014 |

OTHER PUBLICATIONS

Bengio et al., Aseptic Chromatography Processing. Dream or Reality? Annals of the New York Academy of Sciences. May 1996;782(1):432-440. Epub: Dec. 17, 2006. doi: https://doi.org/10.1111/j.1749-6632.1996.tb40581.x.

Blom et al., Efficient chromatographic reduction of ovalbumin for egg-based influenza virus purification. Vaccine. Jun. 24, 2014;32(30):3721-4. doi:10.1016/j.vaccine.2014.04.033. Epub May 5, 2014.

Langhield et al., Chapter 14: Manufacture of measles viruses. Methods Mol Biol. 2011;737:345-66. doi: 10.1007/978-1-61779-095-9_14.

Van Wezel et al., Large-scale concentration and purification of virus suspension from microcarrier culture for the preparation of inactivated virus vaccines. Dev Biol Stand. 1979;42:65-9.

*Primary Examiner* — Agnieszka Boesen
(74) *Attorney, Agent, or Firm* — Wolf, Greenfield & Sacks, P.C.

(57) ABSTRACT

Described herein are processes for the purification of viruses and compositions thereof.

12 Claims, 11 Drawing Sheets

FIG. 18

ASEPTIC PURIFICATION PROCESS FOR VIRUSES

RELATED APPLICATIONS

This application is a continuation of U.S. application Ser. No. 15/561,094, filed Sep. 25, 2017 and issued as U.S. Pat. No. 10,662,412, which is a national stage filing under 35 U.S.C. § 371 of International Application No. PCT/EP2016/057324, filed Apr. 4, 2016, each of which is herein incorporated by reference in its entirety.

FIELD OF INVENTION

The disclosure relates to processes for the purification of viruses.

BACKGROUND

Regulatory agencies such as the World Health Organization establish standards and guidelines for the production of pharmaceutical compositions administered to human, such as vaccines, that limit quantity and components of the compositions. For example, for vaccines, vaccine preparations must be sterile (i.e., free from independently replicating organisms) and contain no more than 10 ng of DNA per human dose, among other requirements. Such standards are in place in order to ensure safety of the composition for human administration, but may introduce challenges in the processes used to produce the compositions.

SUMMARY

Aspects of the invention provide processes for the purification of virus particles comprising the steps of (a) providing a liquid medium comprising a virus particles, wherein the virus particles are greater than about 100 nm in diameter; (b) contacting the virus particles with a solid-phase matrix comprising a ligand-activated core and an inactive shell comprising pores, wherein the molecular weight cut off of the pores excludes the virus particles from entering the ligand-activated core, and wherein a molecule smaller than the molecular weight cut off of the pores can enter the ligand-activated core; and (c) separating the solid-phase matrix from the virus particles by filtration to produce a final virus preparation; wherein the process is performed aseptically.

In some embodiments, the liquid medium comprising the virus particles is subjected to one or more pre-purification step(s) prior to step (b). In some embodiments, the pre-purification step comprises (a) digesting host cell genomic DNA in the liquid medium comprising the plurality of the viruses or virus particles by enzymatic treatment; and/or (b) ultra/diafiltration of the liquid medium comprising the plurality of the viruses or virus particles using a hollow fiber membrane having a pore size equal or greater than 750 kDa.

In some embodiments, the virus particles are about 200 nm, 300 nm, 400 nm, 500 nm or more in diameter. In some embodiments, the virus is a live virus, an attenuated live virus, a modified live virus, or a recombinant live virus. In some embodiments, the virus belongs to a virus family selected from the group consisting of Paramyxoviridae, Orthomyxoviridae, Flaviviridae, Filoviridae, Arenaviridae, Rhabdoviridae, and Coronaviridae. In some embodiments, the virus belongs to the Paramyxoviridae virus family (being live or inactivated). In some embodiments, the virus is measles virus.

In some embodiments, the molecule entering the core of the solid-phase matrix has a molecular weight less than 700 kDa. In some embodiments, the ligand of the ligand-activated core of the solid-phase matrix is capable of binding the molecule that enters the ligand-activated core via cation-, anion-, hydrophobic- or mixed interactions. In some embodiments, the ligand of the ligand-activated core of the solid-phase matrix is octylamine. In some embodiments, the solid-phase matrix is used as a slurry and at a final concentration between 2.5% (v/v) and 30% (v/v), preferably 3.3%, 5%, 6.6% or 10%, most preferably 10%. In some embodiments, the solid-phase matrix is incubated with the liquid medium comprising the virus particles at room temperature (20° C. to 25° C.) with a stirring for at least 1 hour, preferably 2 hours, 3 hours or 4 hours, most preferably 2 hours.

In some embodiments, the relative reduction of impurity of the final virus preparation relative to the liquid medium comprising the plurality of the viruses or virus particles is in a range from 60 to 95%. In some embodiments, the residual impurity of the final virus preparation is less than 1%.

In some embodiments, the filtration of step (c) of claim 1 is performed using a filter having a pore size equal to or greater than 1 μm. In some embodiments, the process is followed by one or more aseptic filtration step(s).

In some embodiments, the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is EB66 cell line.

Aspects of the invention provide a use of any of the processes described herein for manufacturing a composition for immunization against a viral infection.

Other aspects provide compositions comprising the virus particles obtainable by any of the processes described herein for treating and/or preventing a viral infection.

BRIEF DESCRIPTION OF THE DRAWINGS

The accompanying drawings are not intended to be drawn to scale. The Figures are illustrative only and are not required for enablement of the disclosure. For purposes of clarity, not every component may be labeled in every drawing. In the drawings:

FIG. 3A shows a representative silver stained SDS-PAGE gel. FIG. 3B shows a representative Western blot using an anti-EB66-HCP-IgG primary antibody.

FIG. 4A shows a representative silver stained SDS-PAGE gel. FIG. 4B shows a representative Western blot using an anti-EB66-HCP-IgG primary antibody. FIG. 4C shows a representative Western blot using an anti-measles virus fusion protein primary antibody.

FIG. 5A shows NTA of a sample from the harvest of the measles virus. FIG. 5B shows NTA of a diafiltrated sample.

FIG. 18 presents a schematic showing the classification and properties of various virus families (http://www.nlv.ch/Virologytutorials/Classification.htm).

DETAILED DESCRIPTION

Figure 1:
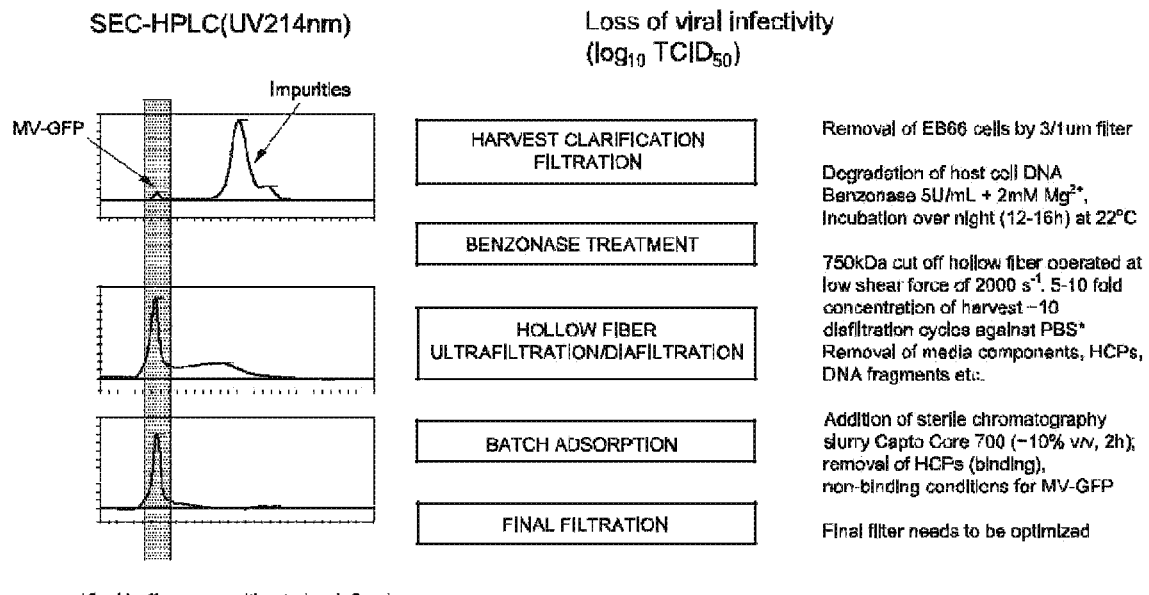
FIG. 1 shows an overview of the purification process of measles virus.

Disclosed herein are aseptic processes for the purification of viruses and compositions comprising purified viruses. In the production of pharmaceutical compositions, such as vaccine compositions, for the administration to subjects, the sterility and safety of the composition must be ensured. Preparation of sterile compositions is typically achieved by subjecting a final composition to sterile filtration, i.e., though a 0.2 μm filter membrane, prior to administration. For compositions, such as viral vaccine compositions, comprising relatively large viruses (i.e., approximately 100 nm or larger), sterile filtration may result in a substantial loss of virus due to it being retained in the membrane, reducing the viral yield from the purification process. Additionally, some viruses, such as measles virus and other viruses that are sensitive to shear stress, each step of the purification process must be performed using gentle conditions, rendering alternative sterilization methods useless. We found that virus purification methods using tangential flow filtration have not been successful and not efficient enough in preparing aseptic compositions of relatively large viruses, such as measles virus (see U.S. Pat. No. 7,759,104 and examples herein). Furthermore, keeping and generating a tangential flow filtration system aseptic is expensive and requires extensive effort. The processes described herein allow for virus preparation under full aseptic conditions resulting in a viral preparation that does not require sterile filtration.

The invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Figure 18:
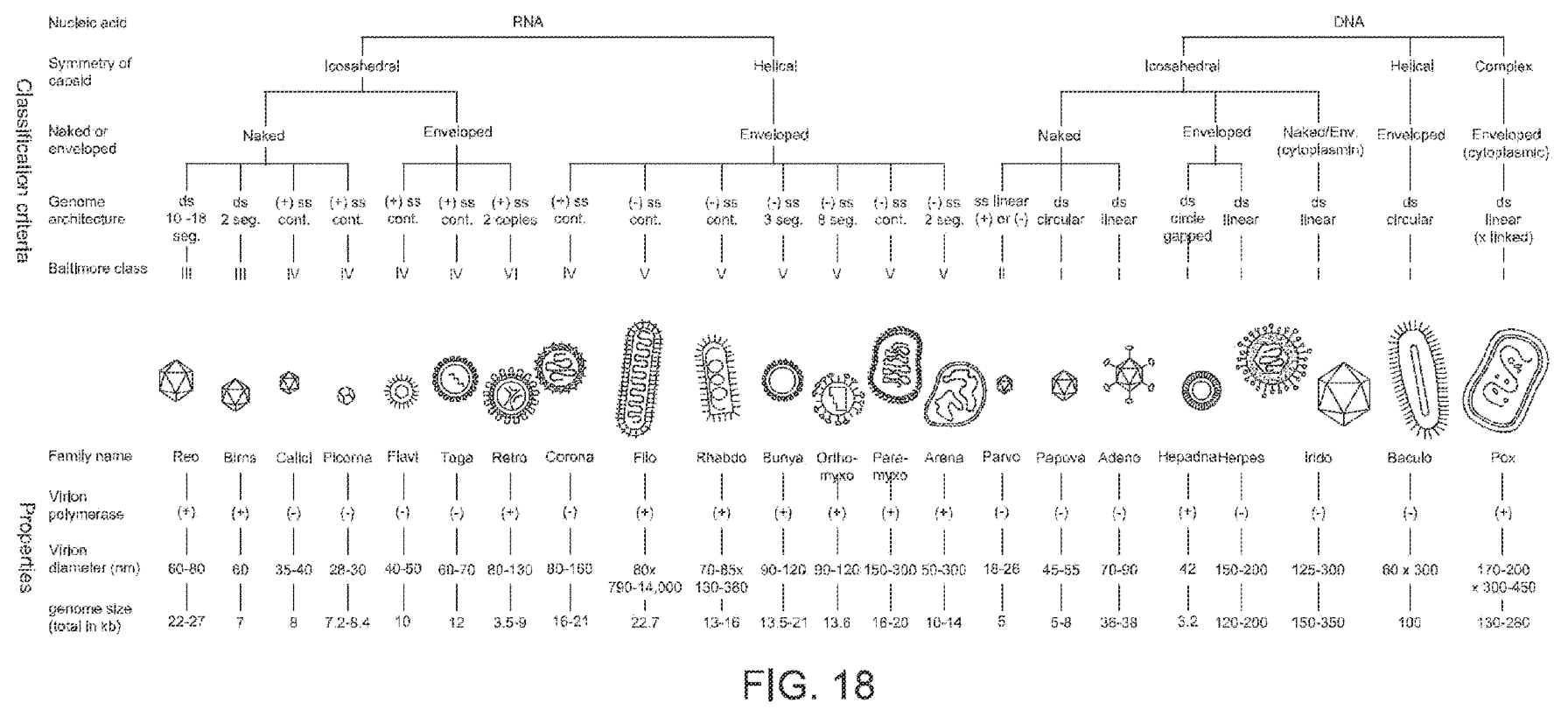

Aspects of the invention relate to processes for purifying a virus. Any virus for which a purified virus preparation is desired may be compatible with aspects of the invention. The terms "virus," "virus particle," "viral particle," and "virion" may be used interchangeably and refer to a virus comprising genetic material surrounded by a protein coat (capsid), and optionally a lipid envelope. In general, viruses may be classified based on the virus genetic material contained within the protein coat and the method by which the virus is able to generate message RNA (mRNA) in an infected cell (a host cell), see FIG. 18. For example, the viruses may be a DNA virus or an RNA virus. In some embodiments, the virus is a retrovirus meaning the virus reverse transcribes its nucleic acid through an intermediate during replication. In some embodiments, the virus is a double stranded DNA (dsDNA) virus, a single stranded DNA (ssDNA) virus, a double stranded RNA (dsRNA) virus, a positive strand single stranded RNA (+ssRNA) virus, a negative strand single stranded RNA (−ssRNA) virus, a single stranded RNA retrovirus (ssRNA-RT), or a double stranded DNA retrovirus (dsDNA-RT).

A virus may also be classified based on the type of host cell that it is capable of infecting. As used herein, a virus is capable of infecting a cell if it is able to enter the cell, replicate and be released from the cell. In some embodiments, the virus may be a killed or inactivated virus. In such examples, the virus is considered to be capable of infecting the host cells that the virus would be capable of entering, replicating, and being released from if the virus was not killed or inactivated. In some embodiments, the virus is capable of infecting eukaryotic cells. In some embodiments, the virus is an animal virus (i.e., capable of infecting animal cells). In other embodiments, the virus is a plant virus (i.e., capable of infecting plant cells).

The processes described herein may be used to purify live viruses or killed or inactivated viruses. In some embodiments, the virus is an attenuated live virus. For example, the virus may have reduced infectivity, virulence, and/or replication in a host, as compared to a wild-type virus. In other embodiments, the virus may have enhanced infectivity, virulence, and/or replication in a host, as compared to a wild-type virus. In some embodiments, the virus is a mutated or modified virus, for example the nucleic acid of the virus may contain at least one mutation relative to the wild-type virus. In some embodiments, the virus is a recombinant live virus, meaning a virus that is generated recombinantly and may contain nucleic acid from different sources. In some embodiments, the virus is sensitive is shear stress. In some embodiments, the virus is handled gently to reduce loss of viral titer and infectivity.

In general, viruses range in size from approximately 20 nm up greater than 1 μm in length. As described herein, viral preparations processes that involve filtration through a 0.2 μm ("sterile filtration"), particularly viral preparations for the administration to subjects, are difficult or not possible for viruses that are approximately 100 nm or larger than the filter pore size. The processes described herein may be used to purify any virus, but may be particularly useful for viruses that are approximately 100 nm or larger in size. In some embodiments, the viruses are on average approximately 100, 150, 200, 250, 300, 350, 400, 450, 500, 550, 600, 650, 700, 750, 800, 850, 900, 950, or approximately 1000 nm in size or larger. In some embodiments, the virus may be a pleomorphic virus, meaning that within a population of the virus, viruses may be present in different sizes and/or shapes. In some embodiments, the virus belongs to the family Paramyxoviridiae, Orthomyxoviridae, Flavivirdae, Filoviridae, Arenaviridae, Rhabdoviridae, or Coronaviridae. In some embodiments, the virus is a virus from the family Retro, Corona, Fil, Rhabdo, Buyna, Orthomyxo, Paramyxo, Arena, Herpes, Irido, Baculo, or Pox. Particularly preferred viruses to be used with the processes described herein is the measles virus, HIV, giant mimivirus, or Herpes virus. In some embodiments, the virus is an attenuated life form, such as an attenuated virus of any of the viruses described herein, for example an attenuated measles virus.

Aspects of the invention described herein relate to aseptic processes for purifying a virus. As used herein, the term "aseptic" refer to compositions, processes, and conditions that are free from any contaminating living organisms. In some embodiments, each step of the process is performed under aseptic conditions such that the resulting virus preparation may be free from independently replicating living organisms.

The processes described herein provide aseptic methods for the purification of viruses through sequential steps that remove impurities or contaminants from the viral preparation. As used herein, "impurities" and "contaminants" may be used interchangeably and refer to undesired components in the viral preparation at any step during the purification process. In some embodiments, impurities or contaminants may be host cells or fragments thereof, including host cell DNA and/or host cell proteins; viral fragments or viral nucleic acid; enzymes, such as BENZONASE® Nuclease, salts; and components of the liquid medium. The term "residual impurity" refers to any amount of remaining impurity or contaminant following one or more steps of the purification process. In some embodiments, residual impurities are the remaining impurities in the final viral preparation.

The processes described herein involve providing a liquid medium comprising a plurality of viruses for purification. Viruses may be produced or provided by any method known in the art. For example, the virus may be produced by propagating in a live host, an embryonic egg, tissue culture or cell line, such as in the EB66® cell line. Selection of the method for producing the virus will depend on various factors such as the virus and type of host cell it is capable of replicating and the amount of virus production desired.

In certain embodiments, the virus is propagated in cell or tissue culture. Any cell that is permissive (capable of being infected with the virus) for entry and replication of the virus can be used for virus propagation. In some embodiments, the cells are primary cells (e.g., cells that have been isolated from a host organism). In some embodiments, the cells are from a cell line. In some embodiments, the cell line is derived from cells of a mammal (such as a human or non-human mammal), a bird, an insect, or a plant. In some embodiments, the cells of the cell line are EB66® cells, Vero cells, Vero-Hisa cells, HeLa cells, HeLa-S3 cells, 293 cells, PC12 cells, CHO cells, 3T3 cells, PerC6 cells, chicken embryonic fibroblasts (CEFs), or diploid avian cells. In some embodiments, the cells of the cell line are cells that grow in suspension and do not adhere. In some embodiments, the diploid avian cells are derived from avian stem cells. In some embodiments, the diploid avian cells are duck cells. In some embodiments, the cells are of the EB66® cell line.

Following viral replication in a cell or cell population, the virus may be released into a liquid medium surrounding the infected cell. In some embodiments, the host cell may be lysed (e.g., enzymatically, mechanically) to release the virus into the liquid medium. The type of liquid medium into which the virus is released will depend on the type of host cell and viral propagation method used. In some embodiments, the liquid medium contains serum, plasma, blood, extracellular fluid, allantoic fluid, amniotic fluid, yolk sac, buffer, or cell or tissue culture medium. Any cell or tissue culture medium that supports growth of the cell or cell population may be used.

In some embodiments, the cells are grown as a monolayer on a culture substrate, such as a flask, dish or plate. In such embodiments, the virus is harvested from the cells by removing the culture medium from the cells. In some embodiments, the cells are lysed to release the virus into the culture medium and the culture medium is collected to harvest the virus. In other embodiments, the cells are grown in suspension in which the cells are floating or only lightly adherent to the culture substrate. In some embodiments, the culture substrate may be a rolling flask, shaker flask, spinner flask, or bioreactor. In yet other embodiments, the cells are grown in a mixed culture in which a portion of the cells are adherent to the culture substrate and a portion of the cells are floating and non-adherent. In some embodiments, the cells and the virus are both present in the liquid medium.

Methods for culturing cells will be evident to one of skill in the art. See, e.g., General Techniques of Cell Culture, Cambridge University Press, Cambridge, United Kingdom.

In some embodiments, the liquid medium containing the virus is subjected to one or more pre-purification steps. In some embodiments, one or more pre-purification steps may be used, for example, to reduce the presence of one or more impurities or contaminants, remove host cells or fragments thereof, enhance virus yield, and/or reduce total processing time.

In some embodiments, any host cells or fragments thereof may be separated or removed from the liquid medium comprising the virus by any suitable means known in the art. In some embodiments, host cells are removed by centrifugation or filtration of the liquid medium. Centrifugation may be performed at a speed and duration that results in separation of host cells or fragments thereof from the virus. For example, the host cells or fragments thereof form a pellet while the virus remains in the liquid medium. Alternatively or in addition, filtration methods, such as membrane filtration, may be used to remove host cells or fragments thereof from the liquid medium containing the virus (e.g., ultrafiltration). In some embodiments, a filter membrane is selected such that the virus is able to pass through the filter but host cells and fragments thereof remain trapped in the membrane.

In some embodiments, the one or more pre-purification steps involve degrading host cell genomic DNA in the liquid medium comprising the virus. In some embodiments, the host cell genomic DNA is degraded by enzymatic treatment. Any DNA degrading enzyme may be compatible with the processes described herein. In some embodiments, the enzyme is a nuclease. In some embodiments, the nuclease degrades both DNA and RNA. Non-limiting examples of nucleases include, without limitation, BENZONASE®, DNAse I, DNAse II, Exonuclease II, micrococcal nuclease, nuclease P1, nuclease S1, phosphodiesterase I, phosphodiesterase II, RNAse A, RNAse H, RNAse T1, or T7 endonuclease. In some embodiments, the DNA degrading enzyme treatment reduces or eliminates the presence of DNA fragments larger than about 200 base pairs in length. The enzyme concentration, incubation time, and temperature to degrade nucleic acid in the liquid medium comprising the virus will be evident to one of skill in the art. In some embodiments, the ion concentration (e.g. $Mg^{2+}$, $Mn^{2+}$) and/or pH of the liquid medium comprising the virus may also be optimized to enhance or reduce activity of the enzyme. DNA degrading enzymes may be isolated or obtained from any source known in the art, for example the enzyme may be a microbial, plant, or mammalian enzyme; recombinantly produced; and/or commercially available.

In some embodiments, the one or more pre-purification steps involve ultrafiltration and/or diafiltration of the liquid medium comprising the virus. As used herein, "ultrafiltration" refers to a method of separating components of a mixture based on the size or molecular weight of the components by passing the liquid medium through a semipermeable membrane. Components that have a larger molecular weight than the pore size (the molecular weight cutoff (MWCO)) of the semi-permeable membrane are retained on the membrane, while components of smaller molecular weight are allowed to pass through the membrane. As used herein, "diafiltration" refers to a method of reducing the concentration of a component, such as an impurity or contaminant, in a mixture, and/or exchanging buffers. Diafiltration may be performed by any of a number of methods, for example, continuous diafiltration, discontinuous diafiltration, or sequential diafiltration. In some embodiments, ultrafiltration and diafiltration methods are performed concurrently or sequentially.

In some embodiments, the ultrafiltration and diafiltration are performed using tangential flow filtration. As used herein, "tangential flow filtration," also referred to as "cross flow filtration," is a filtration method in which the feed stream (i.e., the liquid medium containing the virus) is tangential to the filter membrane. In some embodiments, the tangential flow filtration is performed using a hollow fiber membrane. The feed stream is fed into the tubular fiber and components of the feed that are smaller than the MWCO of the membrane are allowed to pass through and out of the stream, whereas larger components are maintained in the stream and may be recirculated through the system. Additional liquid medium or an alternative buffer may be continuously added to the stream at the same rate as removal of small components of the mixture, thereby maintaining a consistent concentration of the virus. In some embodiments, the liquid medium comprising the virus is subjected to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or at least 30 volume exchanges of liquid medium or an alternative buffer. Non-limiting examples of alternative buffers include phosphate buffered solution (PBS), Dulbecco's phosphate-buffered saline (DPBS), Earle's balanced salt solution (EBSS), Hank's balanced salt solution (HBSS), or water.

In some embodiments, the MWCO of the membrane is at least 500 kilodaltons (kDa), 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, or at least 900 kDa. In some embodiments, the MWCO of the membrane is greater than or equal to 750 kDa.

Aspects of the disclosure relate to contacting the liquid medium comprising the virus with a solid-phase matrix. In some embodiments, the liquid medium comprising the virus is contacted with a solid-phase matrix by batch adsorption. As used herein, "batch adsorption" refers to a method in which a solid-phase matrix is added to a liquid phase mixture of components (e.g., the liquid medium comprising the virus) including a molecule for which purification is desired (e.g., a virus). In some embodiments, the solid-phase matrix is suspended in a buffer solution referred to as a slurry. The solid-phase matrix adsorbs components of the mixture. Subsequently, the solid-phase matrix and the adsorbed components may be separated from the mixture using any method known in the art, such as centrifugation, filtration, or flocculation. In some embodiments, the molecule for which purification is desired (e.g., a virus) is adsorbed to the solid-phase matrix. In other embodiments, impurities or contaminants are adsorbed to the solid-phase matrix and the molecule for which purification is desired remains in the liquid phase. General batch adsorption methods and considerations can be found, for example, in Protein Purification: Principles and Practice, $3^{rd}$ Edition, Springer Advanced Texts in Chemistry, New York, N.Y.

In some embodiments, the solid-phase matrix comprises a matrix and a ligand that binds components of a mixture. In some embodiments, the matrix is SEPHAROSE® or agarose, such as highly cross-linked agarose. In some embodiments, the solid-phase matrix comprises a ligand-activated core containing the ligand that binds components of a mixture and an inactive shell. In some embodiments, the inactive shell surrounds the matrix and the core ligand and comprises pores with a MWCO. In general, the pores of the inactive shell prevent binding of the virus with the ligand of the solid-phase matrix and allow entry of components of size less than the MWCO to enter the inactive shell and interact with the ligand. In some embodiments, the MWCO of the inactive shell is at least 500 kilodaltons (kDa), 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, or at least 900 kDa. In some embodiments, the MWCO of the inactive shell is greater than or equal to 700 kDa. In some embodiments, the pores of the inactive shell allow entry of impurities into the ligand-activated core of the solid-phase matrix. In some embodiments, impurities interact with or bind to the ligand-activated core. In some embodiments, the impurities may interact with or bind to the ligand-activated core by any type of interaction known in the art. In some embodiments, the impurities may interact with or bind to the ligand-activated core by cation, anion, hydrophobic, or mixed interactions.

In some embodiments, the ligand of the solid-phase matrix is octylamine, diethylaminoethyl, quaternary ammonium, or sulfonate. Non-limiting examples of solid-phase matrices that may be compatible with the processes described herein include, without limitation, CAPTO® Core 700, CAPTO® DEAE, CAPTO® MMC, CAPTO® Q, CAPTO® S, FRACTOGEL® TMAE, Hyx T II, Q SEPHAROSE® Fast Flow. In some embodiments, the solid-phase matrix is CAPTO® Core 700.

In some embodiments, the solid-phase matrix is suspended in a buffer solution as a slurry prior to combining with the liquid medium comprising the virus. In some embodiments, the solid-phase matrix is combined with the liquid medium comprising the virus as a slurry at a final concentration between 2.5% (v/v)-30% (v/v), 5% (v/v)-20% (v/v), or 7.5% (v/v)-15% (v/v). In some embodiments, the slurry is added at a final concentration of approximately 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 10.5%, 11%, 12%, 13%, 14%, 15%, 16%, 17%, 18%, 19%, 20%, 21%, 22%, 23%, 24%, 25%, 26%, 27%, 28%, 28%, 29%, or 30% (v/v). In some embodiments, the slurry is added at a final concentration of approximately 10% (v/v).

Conditions, including the duration, temperature, and mode of contact between the solid-phase matrix and the liquid medium comprising the virus, may be varied in order to enhance recovery of the virus and enhance binding and removal of impurities from the liquid medium. In some embodiments, the solid-phase matrix is contacted or incubated with the liquid medium comprising the virus at a temperature between 15° C.-30° C., such as 17° C.-27° C., or 20°-25° C. In some embodiments, the solid-phase matrix is contacted or incubated with the liquid medium comprising the virus at room temperature. In some embodiments, the solid-phase matrix is contacted or incubated with the liquid medium comprising the virus at a temperature of 15° C., 16° C., 17° C., 18° C., 19° C., 20° C., 21° C., 22° C., 23° C., 24° C., 25° C., 26° C., 27° C., 28° C., 29° C., or 30° C.

In some embodiments, the solid-phase matrix is contacted or incubated with the liquid medium comprising the virus for a duration between 1 and 5 hours, 1 and 10 hours, 1 and 24 hours, 5 and 10 hours, 10 and 15 hours, or between 15-24 hours. In some embodiments, the solid-phase matrix is contacted or incubated with the liquid medium comprising the virus for approximately 1, 2, 3, 4, 5, 6, 7, 8, 9, 10, 11, 12, 13, 14, 15, 16, 17, 18, 19, 20, 21, 22, 23, or 24 hours. In some embodiments, the solid-phase matrix is contacted or incubated with the liquid medium comprising the virus for approximately 2 hours.

In any of the embodiments described herein, the solid-phase matrix may be contacted or incubated with the liquid medium comprising the virus by any mode known in the art. For example, the solid-phase matrix and liquid medium comprising the virus may be contacted or incubated in a vessel statically or with shaking, inversion, oscillation, or stirring. In some embodiments, the solid-phase matrix and liquid medium comprising the virus are incubated with stirring.

Following batch adsorption, the solid-phase matrix and any bound components may be removed from the liquid phase by any method known in the art, such as centrifugation, filtration, or flocculation. In some embodiments, the solid-phase matrix and any bound components are removed by filtration, such as by any of the filtration methods described herein. In some embodiments, the solid-phase matrix and any bound components are removed by membrane filtration using a membrane with a pore size of at least 0.5, 0.6, 0.7, 0.8, 0.9, 1, 1.1, 1.2, 1.3, 1.4, 1.5, 1.6, 1.7, 1.8, 1.9, or at least 2.0 µm. In some embodiments, the pore size of the membrane is greater than or equal to 1.0 µm. The solid-phase matrices used in the processes described herein may be regenerated (e.g., cleaned and re-sterilized) and used for batch adsorption again.

Virus preparations produced using any of the processes described herein may be further subjected to additional processing steps, including additional filtration steps and/or lyophilization. The virus preparation may also be subjected to analysis for purity of the preparation. For example, the virus preparations may also be assessed for the presence of impurities and contaminants, host cell genomic DNA, and/or host cell proteins. The purity of a virus preparation may be assessed using any method known in the art, such as size exclusion chromatography (SEC), optical density at different wavelengths, protein gel electrophoresis (e.g., SDS-PAGE), Western Blotting, ELISA, PCR, and/or qPCR.

In some embodiments, the virus preparation is assessed for the amount of residual impurities or contaminants. In some embodiments, the amount of residual impurities or contaminants is compared to the amount of impurities or contaminants at an earlier stage in the purification process. In some embodiments, the relative reduction of impurities in the final virus preparation is between 60-95% relative to the presence of impurities at an earlier stage in the purification process. In some embodiments, the relative reduction of impurities in the final virus preparation is approximately 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%. In some embodiments, the final virus preparation contains less than 5% impurities or contaminants. In some embodiments, the final virus preparation contains less than 5, 4, 3, 2, 1, 0.9, 0.8, 0.7, 0.6, 0.5, 0.4, 0.3, 0.2, or less than 0.1% impurities. In some embodiments, the final virus preparation contains less than 1% impurities.

Any of the processes described herein may be used in the manufacture of a composition comprising purified virus for administration to a subject. In some embodiments, the subject is a mammalian subject, such as a human or a non-human animal, including livestock, pets or companion animals. In some embodiments, the composition may be administrated to a subject in need of immunization against the virus or similar virus as that of the virus preparation. In some embodiments, the virus preparations or compositions comprising viruses purified using the processes described herein are for treating or preventing infection with the virus or a similar virus as that of the virus preparation.

The virus preparations or compositions viruses purified using the processes described herein may be administered to a subject by any route known in the art. In some embodiments, the preparations or compositions may be administered via conventional routes, such as parentally. As used herein, "parental" administration includes, without limitation, subcutaneous, intracutaneous, intravenous, intramuscular, intraarticular, intrathecal, or by infusion.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Development of a Purification Process for Live Measles Virus Vaccine Produced in EB66 Cells A downstream purification process was developed for the attenuated measles virus vaccine produced on the EB66® cells.

Clarification of Infected Cell Culture Media

Following production of the virus in cell culture, the cells were removed by filtration. Both depth filtration and membrane filtration as well as suitable separation ranges (depth filtration) and pore size (membrane filtration) were evaluated for removal of the cells from the cell culture supernatant without significant loss of viral particles. A combination filter containing 3 µm/1 µm (Parker PLPLK-01DD-PNL-S) was used to separate cells from virus particles. Following filtration, no EB66® cells were detected in the clarified supernatant by visual microscopic analysis.

DNA Removal

The endonuclease BENZONASE® was used to remove gDNA from the clarified harvest cell culture supernatant (the "harvest"). Various enzyme concentrations, temperatures and time were evaluated. A minimum concentration of 1 to 2 mM $Mg^{2+}$ or $Mn^{2+}$ was also added to the harvest with the enzyme. The pH of the mixture was maintained between 7.2 to 8.0. The quantity and size of any remaining DNA, as well as any loss of viral infectivity, was tested at various time points.

A final enzyme concentration of 5 U/ml was used in an over-night incubation (~12-16 hrs) at room temperature (18-22° C.) for DNA degradation. The remaining DNA content and size was analyzed by qPCR for 90, 176 and 316 bp amplicons. Using these methods, the total amount of host cell DNA (HCD) was reduced from 440 ng to 0.5 ng for DNA greater than 317 bp in size and from 1400 ng to 2 ng for DNA greater than 176 bp in size (Table 1).

Purification of Measles Virus by Tangential Flow Filtration

A tangential flow filtration (TFF) system based on hollow fiber and corresponding process parameters were applied to minimize shear forces and avoid disruption of the viral envelope and loss of viral infectivity. Various lumen diameters (0.5 to 1.0 mm) and recirculation flow rates were found to have shear rates of between 1000 to 6000 $s^{-1}$. The membrane cut-off was optimized to allow complete retention of measles virus while various impurities (proteins, DNA fragments, media components) were allowed to pass through the membrane. The process was performed at room temperature, therefore the process time was also taking into consideration.

The clarified and BENZONASE® treated harvest was concentrated 5-10 fold using a 750 kDa hollow fiber membrane (GE Healthcare) at a flow rate corresponding to a shear rate of 2000 $s^{-1}$. Following concentration, approximately 10 diafiltration cycles were performed using PBS buffer to remove remaining impurities (e.g., media components, host cell proteins (HCP), DNA fragments). Excipients for virus stabilization (i.e., for subsequent lyophilization) can be added in the diafiltration buffer directly or added as stock solution to the concentrated viral bulk. Despite the gentle conditions applied in the process described above, the total loss of viral infectivity was nearly 1 log TCID50 (50% Tissue Culture Infective Dose).

Purification of Measles Virus by Batch Adsorption

An optional batch adsorption process step was developed that could be applied after ultra/diafiltration step. Various chromatography resins with different ligands (cation-, anion-, hydrophobic and mixed mode) were assessed for binding residual impurities (e.g., HCPs, DNA fragments) while measles virus was maintained in the supernatant. Use of CAPTO® Core 700 resin (GE Healthcare) resulted in further reduction of HCPs with a high recovery of MV-GFP (a live attenuated measles virus (Schwartz strain) encoding green fluorescent protein). CAPTO® Core 700 resin is composed of a ligand-activated core and inactive shell. The inactive shell excludes large molecules (MWCO approximately 700 kDa) from entering the core through the pores of the shell. Larger molecules are therefore collected in the supernatant while smaller impurities bind to the internal ligands of the resin. The core of each bead of the resin is functionalized with ligands that are both hydrophobic and positively charged, resulting in a highly efficient multimodal binding of various impurities small enough to enter the core. The final slurry concentration after addition was optimized to 10% v/v. After addition of the CAPTO® Core 700 medium, residual HCP can be further reduced. Interestingly, remaining DNA fragments did not bind to the resin. Assessment of the remaining impurities and viral infectivity are presented in Table 1.

Final Polishing by Filtration

A final polishing step was performed by membrane filtering concentrated viral bulk with or without CAPTO® Core 700 resin. Membrane filters with pore sizes in the range of 1-2 µm were evaluated, and recovery of virus particles was assessed.

TABLE 1

Removal of impurities throughout the purification process

| Sample | hcDNA by qPCR (ng/mL) | | | HCP by ELISA µg/mL | Residual Benzonase ng/mL | Viral Infectivity concentration $Log_{10}$ $TCID_{50}$/mL | Total Infectivity $Log_{10}$ $TCID_{50}$ |
|---|---|---|---|---|---|---|---|
| | 90 bp | 176 bp | 317 bp | | | | |
| MV Harvest RG25 (starting volume ~1 L) | 4003 | 1400 | 440 | 208 | — | 6.60 | 9.60 |
| Clarified Harvest RG25 + Benzonase | 11 | 2.0 | 0.5 | — | Addition of 5 U/mL* | 6.74 | 9.74 |
| UF/DF Retentate (0.2 L) (5x concentrated, 10 diafiltration cycles) | 14 | 3.7 | 1.2 | 31 | | 6.50 | 8.80 |
| Supernatant after batch adsorption (0.22 L) (Drug substance before final filtration) | 14 | 3.8 | 1.2 | <10 | | 6.17 | 8.51 |

Methods

Size Exclusion Chromatography

Figure 2:
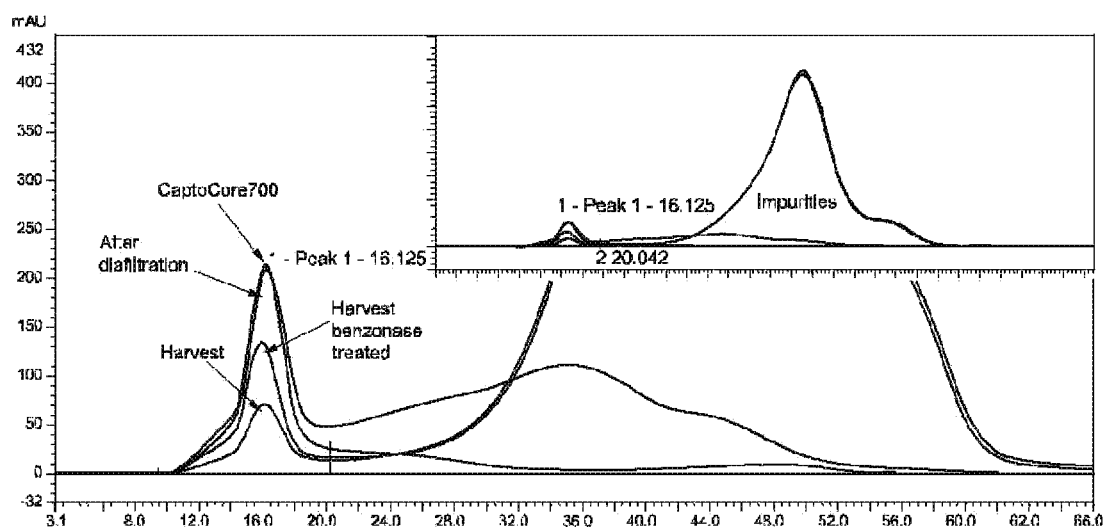
FIG. 2 shows size exclusion chromatography (SEC) traces for the measles virus at different purification steps. The insert shows the SEC traces for both the measles virus (left peak) and impurities (right peak).
Figure 3A:
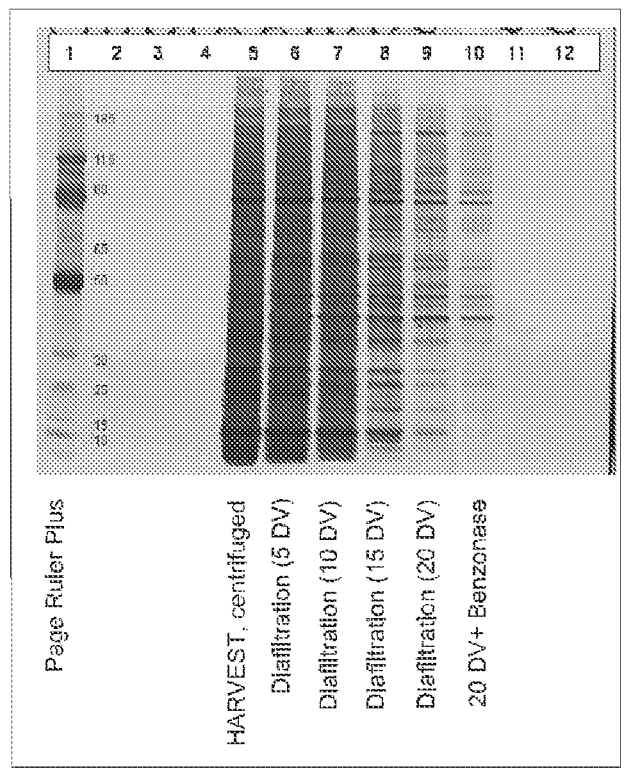
FIGS. 3A-3B shows the presence of host cell proteins (HCP) in samples during various stages of the purification process.
Figure 3B:
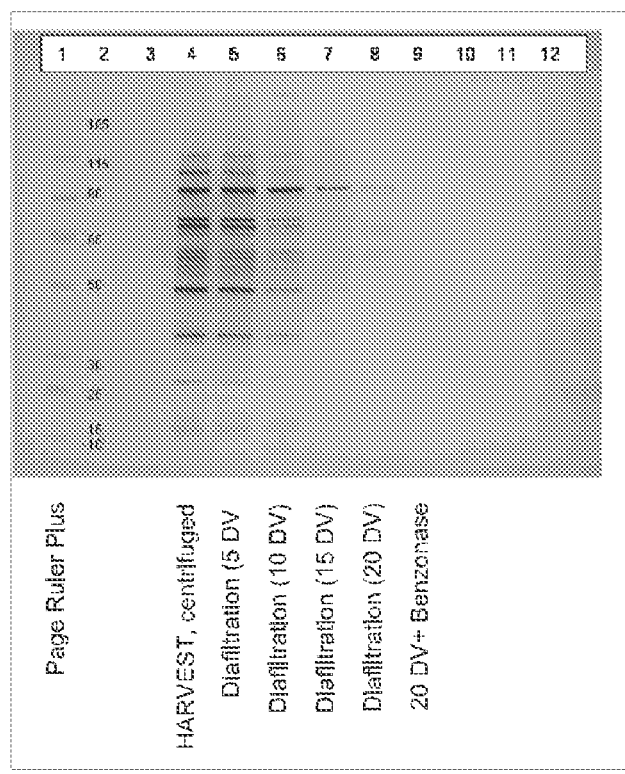

Size exclusion chromatography (SEC) was used to determine the purity of the virus throughout the purification process relative to impurities (e.g. HCP, DNA) which also generate UV absorption. FIG. 2 and Table 2 present an approximation of viral purity throughout the purification process. A significant reduction of impurities (primarily host cell proteins) was observed.

Figure 6:
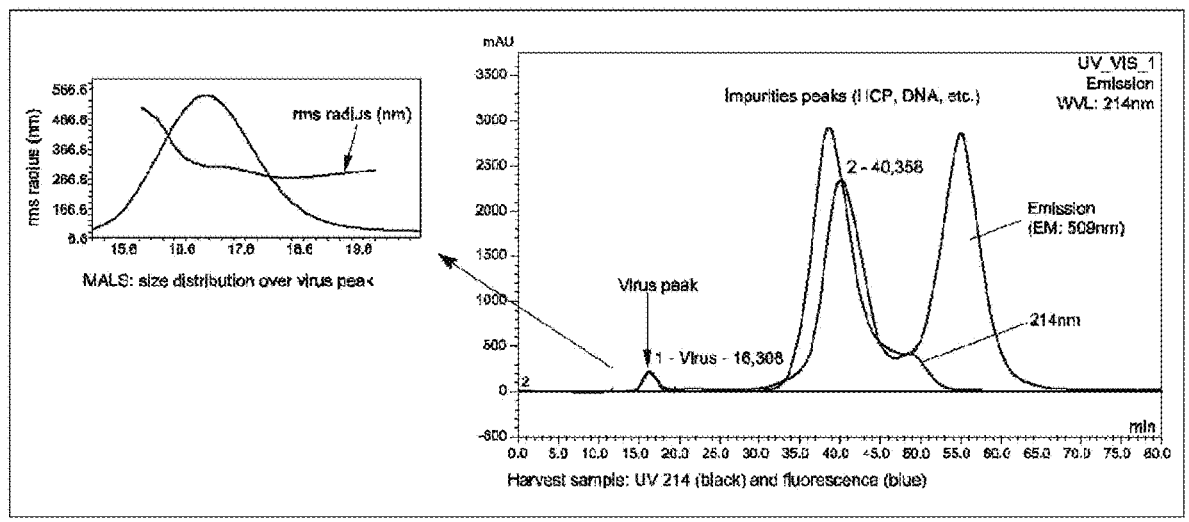
FIG. 6 shows a size exclusion chromatogram (fluorescence signal and $UV_{214\ nm}$; right panel) and virus size determination by multi-angle static light scattering (MALS; left panel) of a sample from the harvest of the measles virus (MV-GFP).
Figure 7:
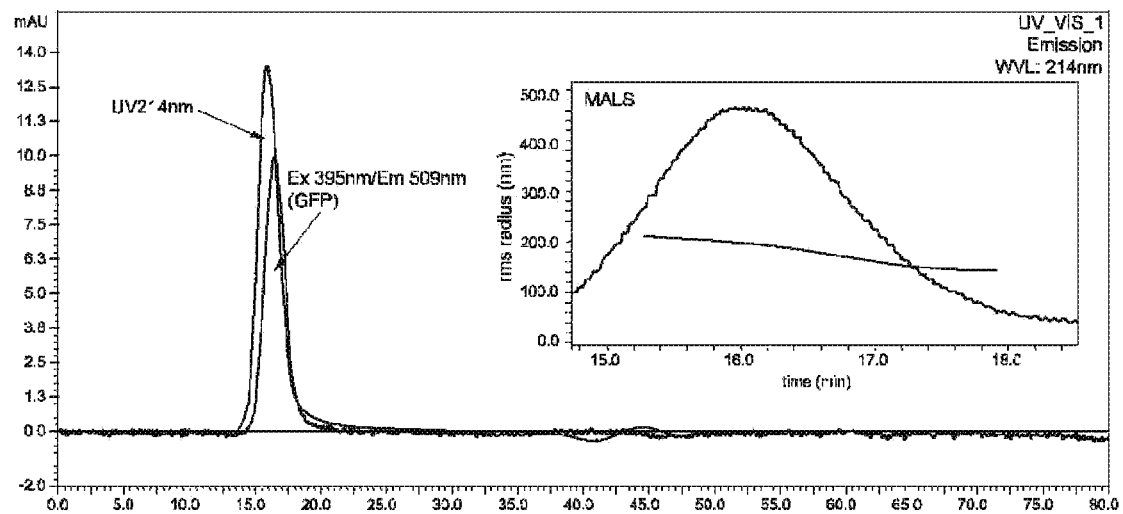
FIG. 7 shows a size exclusion chromatogram (fluorescence signal and $UV_{214\ nm}$) and virus size determination by multi-angle static light scattering (MALS; inset) of a highly purified measles virus (MV-GFP) sample.

SEC in conjunction with UV absorption (at various wavelengths) and fluorescence emission (specific for GFP) was applied for virus analysis. Briefly, separation was performed on a Sephacryl S500 column (10×300 mm; separation range up to 20 Mio Da) in PBS buffer supplemented with 250 mM sodium chloride at a flow rate of 0.5 mL/min. UV signals were recorded at 214 nm, 280 nm and 260 nm. Fluorescence was detected at a wavelength of EM509 nm (EX395 nm) which is specific for GFP. Additional data regarding virus size was collected by connecting the SEC to a multi-angle static light scattering (MALS) detector. Viral particle size was measured by a miniDAWN® TREOS® instrument (Wyatt). An exemplary chromatogram of a harvest sample is shown in FIG. 6, and a highly purified virus preparation is shown in FIG. 7.

TABLE 2

Size Exclusion chromatography analysis of traces presented in FIG. 2

| Sample | Purity acc. to SEC (214 nm) (area virus peak vs. total area) |
|---|---|
| MV Harvest RG25 | 1% |
| Clarified Harvest RG25 + Benzonase | 3% |
| UF/DF Retentate (5x concentrated, 10 diafiltration cycles) | 43% |
| Supernatant after batch adsorption | 70% |

SDS-PAGE and Western Blot

Figure 4A:
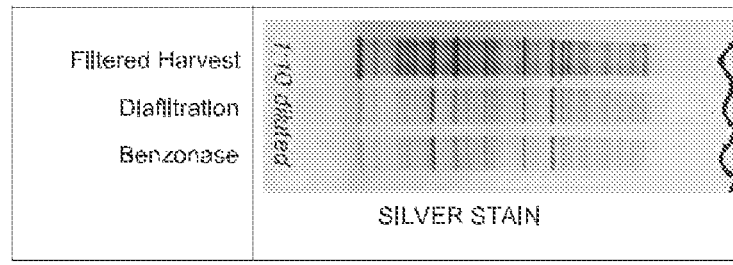
FIG. 4A-4C show monitoring of the presence of HCP in samples after diafiltration and BENZONASE® treatment.
Figure 4B:
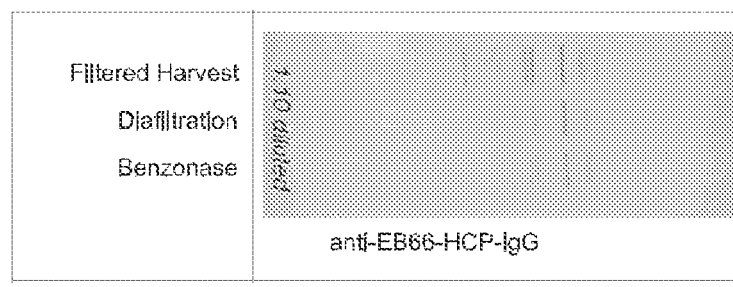
Figure 4C:
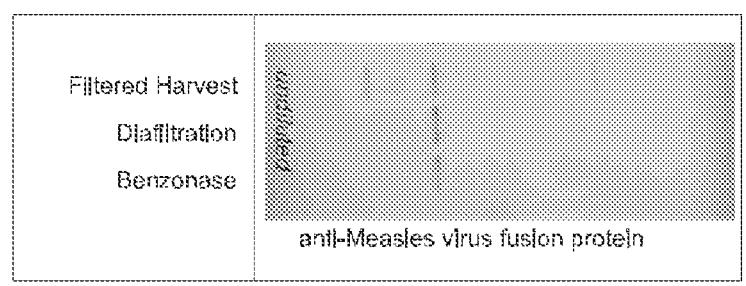

In addition to a quantitative ELISA presence and reduction of host cell proteins throughout the purification process was monitored qualitatively by SDS-PAGE and Western Blotting on (FIGS. 3A, 3B, 4A, and 4B). Additionally, the presence of viral proteins was monitored by using specific antibodies (FIG. 4C).

Briefly, reduced samples were separated on 4-12% Bis-Tris gel for 50 minutes at 200V. Silver stained or non-stained gels were transferred to a nitrocellulose membrane for Western blotting. HCP or virus protein was detected with appropriate antibodies (anti-EB66®-HCP-IgG or anti-Measles virus fusion protein (F), respectively). Anti-rabbit IgG-HRP conjugate was used as secondary antibody.

Nanoparticle Tracking Analyses

Figures 5A, 5B:
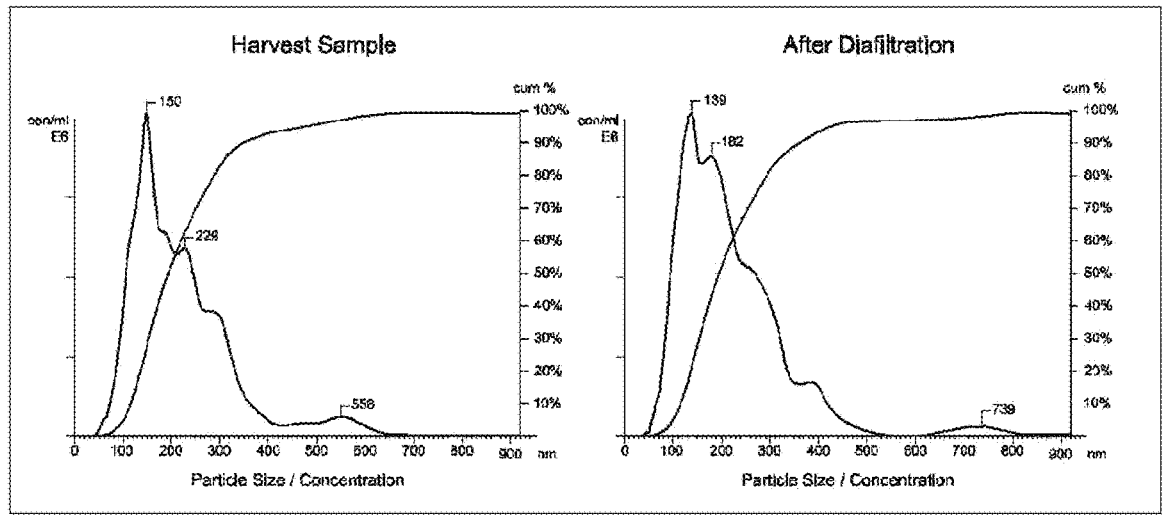
FIGS. 5A and 5B present nanoparticle tracking analyses (NTA) of measles virus during the purification process.

Nanoparticle tracking analyses (NTA) were used to determine the concentration and size of virus particles using a NanoSight instrument. Changes in particle size during downstream process (DSP) may be indicative for loss of integrity of the viral particles. The particle size of the virions was found to be in the range of ~100-400 nm according to NTA (FIGS. 5A-5B). The size distribution was not uniform but showed significant pleomorphism (in accordance with literature) but stayed nearly constant throughout the purification. Tracking analysis graphs of harvest and after diafiltration showed no significant changes in particle size distribution as illustrated in FIGS. 5A-5B.

Quantifying Host Cell DNA (HCD)

The residual host cell DNA from EB66® was determined by qPCR. Briefly, three different partially overlapping fragments of LINE (long interspersed nucleotide elements) were amplified (90, 176 and 319 bp) (see, for example Walker et al., (2004) Genomics 83:518-527). LINE are a variable repetitive sequences present in numerous copies in the duck genome. Quantification of EB66® residual host cell DNA was performed by amplification of the 176 bp fragment. The other two qPCR amplicons (90 and 316 bp) were used to determine the size distribution of the residual host cell DNA from EB66®. The limit of quantification (LOQ) of the three amplifications was 0.01 ng/mL and the coefficient of variation (CV) for the amplification of the 176 bp fragment was 21.3%, as determined in the assay validation.

Assessing Host Cell Proteins

The presence of residual host cell protein (HCP) from EB66® was determined by ELISA. Briefly, purified polyclonal rabbit antibodies were obtained by immunizing rabbits with EB66® whole cell lysate and affinity purified with EB66-HCP coupled to SEPHAROSE® and used for detection of residual HCP. Micro-titer plates were coated with the polyclonal antibodies and then incubated with test samples and controls. Captured EB66® proteins were detected with a biotinylated polyclonal rabbit secondary antibodies. The dynamic range of the assay was from 5-1280 ng/mL, and the CV of the assay was 9.2%, as obtained from the control chart.

Residual Benzonase Detection

Residual BENZONASE® was determined using a commercially available ELISA kit (Benzonase ELISA II, Art. 1.01681 from Merck). Briefly, pre-coated micro-titer plates were used to capture residual BENZONASE® which was detected with an HRP-coupled detection antibody. The limit of detection for the ELISA was 0.1 ng/mL.

The purification process MV-GFP showed efficient removal of host cell DNA. The beginning host cell DNA content of the harvest was 1400 ng/mL for the 176 bp amplicon and 440 ng/mL for the 317 bp amplicon. Host cell DNA was efficiently removed by Benzonase treatment and remained nearly constant throughout the subsequent purification steps. According to qPCR analysis of the 176 bp amplicon, the residual host cell DNA concentration after ultrafiltration/diafiltration was less than 4 ng/mL. The larger DNA fragments, as analyzed by the 317 bp amplicon, were approximately 1 ng/mL. Application of batch chromatography did not further reduce the content of residual DNA. Final compositions that are administered to subjects are adjusted to at least $10^3$ TCID50/dose. Additional dilution of the virus preparation (~$10^6$ TCID50) may be required and would reduce the final content of host cell DNA to an estimated amount of approximately 0.4 to 0.04 ng/dose.

The final concentration of host cell protein determined by ELISA was less than 10 μg/mL, which would also be further reduced to less than 1 μg per dose. Detection and quantification of BENZONASE® using the BENZONASE® ELISA II assay suggest that residual BENZONASE® may be removed efficiently throughout the purification process, resulting in a final concentration below the detection limit of the assay (<0.1 ng/mL).

Example 2: Optimization of the Batch Adsorption Chromatography Step

Figure 8:
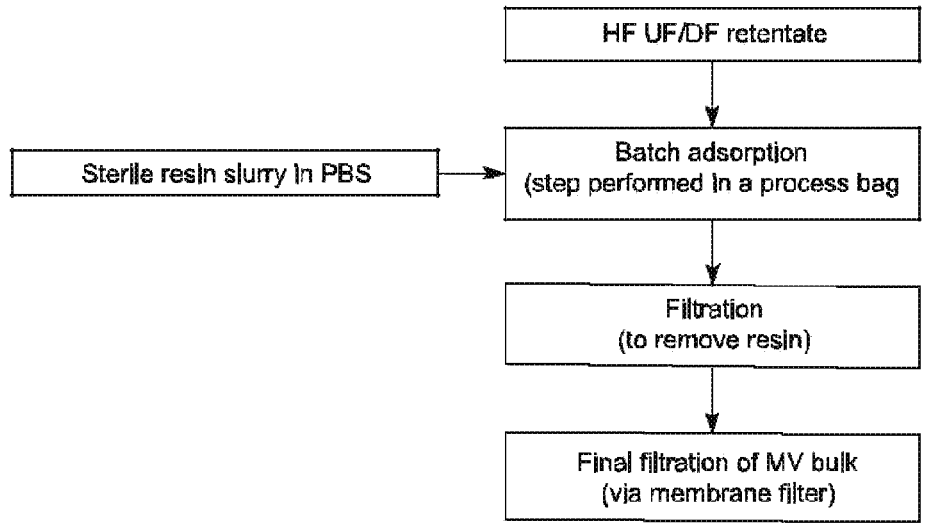
FIG. 8 presents a flow diagram for batch adsorption after ultrafiltration/diafiltration to reduce impurities from the virus preparation.
Figure 9:
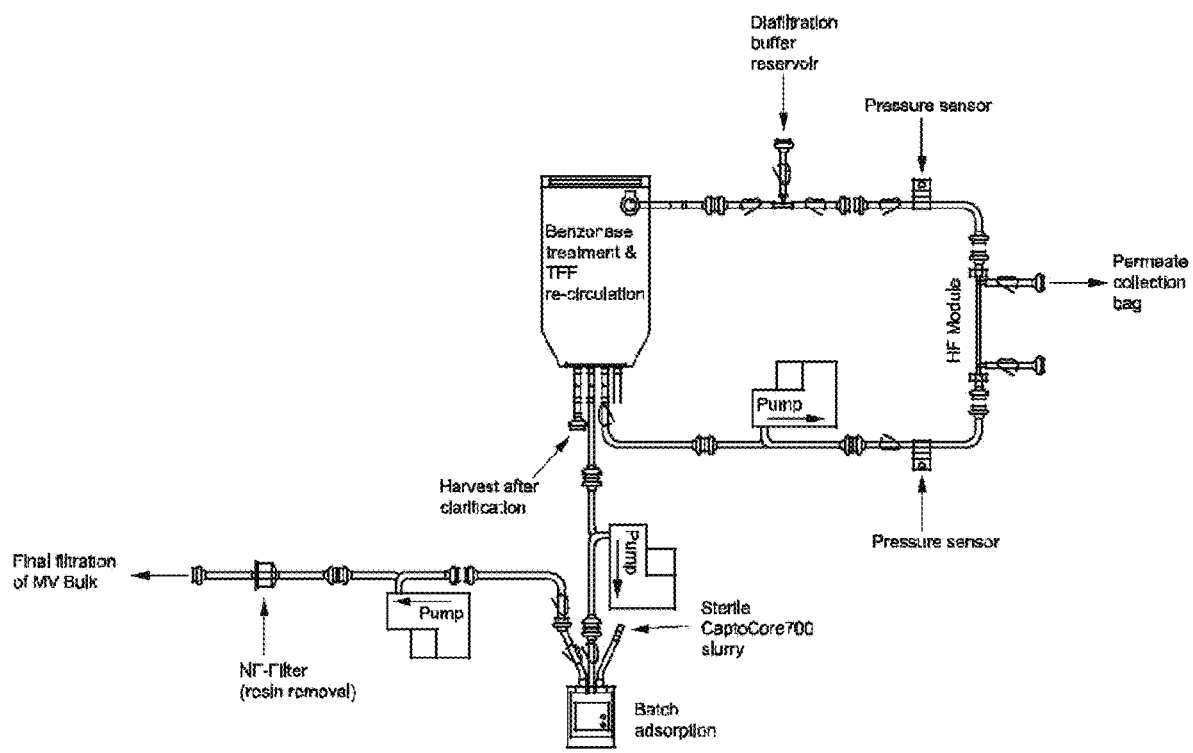
FIG. 9 shows a schematic of the pre-sterilized process assembly.

To further reduce residual impurities in MV-GFP material after the ultra/diafiltration step batch adsorption with a chromatography resin as adsorbent was developed. Batch adsorption is a single stage step and involves adding the adsorbent (resin) to the MV-GFP material in a suitable mixing container and incubating for a defined period of time. The adsorbent is subsequently removed, for example, by filtration or centrifugation. The adsorbent can be introduced aseptically into a process bag after sterilization of the adsorbent by autoclave. A process flow diagram is shown in FIG. 8. The process assembly, including batch adsorption, is diagrammed in FIG. 9.

Screening of Resins for Batch Adsorption

To identify a suitable resin for reduction of residual impurities a screening of various chromatography resins with different ligands (cation-, anion-, hydrophobic and mixed mode) was performed in small scale. The resins tested included CAPTO® Core 700, CAPTO® DEAE, CAPTO® MMC, CAPTO® Q, CAPTO® S, FRACTOGEL® TMAE, Hydroxyapatite Type II and QSFF.

Each of the different chromatography resins was prepared as 50% slurry in PBS and was added 10% v/v to MV-GFP harvest following ultrafiltration/diafiltration. All samples were incubated overnight at 4° C. The resins were removed by centrifugation. The supernatants were analyzed by size-exclusion chromatography, as described in Example 1. The CAPTO® Core 700 resin showed a significant reduction of residual impurities (HCPs) while retaining a high recovery of MV-GFP (Table 3).

TABLE 3

Screening of chromatography resins for selection of the solid-phase matrix

| Resin* | recovery MV-GFP [%] | recovery impurities [%] |
|---|---|---|
| CaptoCore700 | 100 | 39 |
| CaptoDEAE | 89 | 73 |
| CaptoMMC | 95 | 66 |
| CaptoQ | 77 | 69 |
| CaptoS | 101 | 100 |
| FractogelTMAE | 48 | 53 |
| Hyx T II | 74 | 50 |
| QSFF | 84 | 67 |

Figure 10:
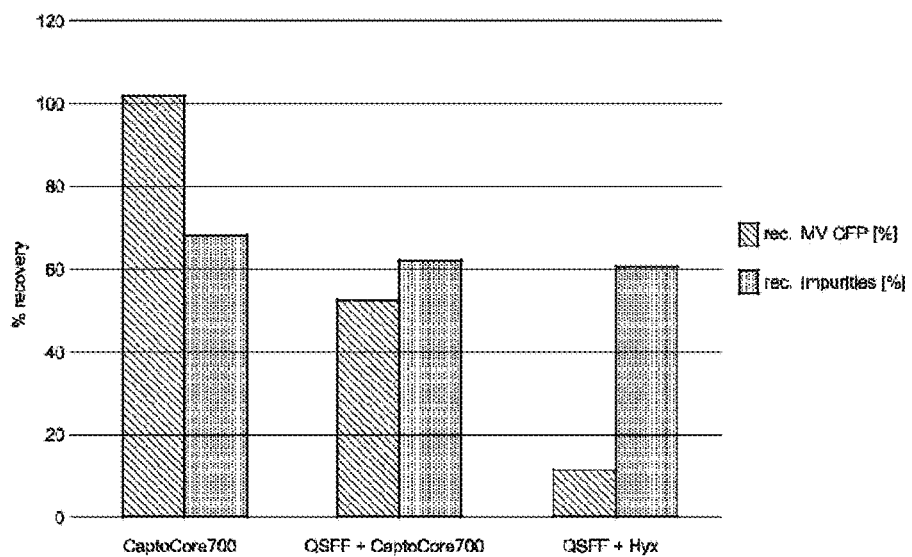
FIG. 10 presents percent recoveries of virus (rec. MV GFP; striped) and impurities (solid gray) as assessed by size exclusion chromatography following batch adsorption using CAPTO® Core 700 resin or a combination of CAPTO® Core 700 and QSFF resins or CAPTO® Core 700 and Hydroxyapatite (Hyx) resins.

Combinations of resins were also evaluated, including CAPTO® Core 700 with QSFF and CAPTO® Core 700 with Hydroxyapatite (Hyx T II). 50% slurries of each of CAPTO® Core 700 and the combinations were prepared in PBS and added 10% v/v to the UF/DF MV-GFP harvest. The samples were incubated for 2 hours at room temperature. The resins were removed by centrifugation, and the supernatants were analyzed by size-exclusion chromatography. Although use of CAPTO® Core 700 resin resulted in a reduction of residual impurities (HCPs) while retaining a high recovery of MV-GFP, the combinations of CAPTO® Core 700 and QSFF and CAPTO® Core 700 and Hyx did not improve reduction of residual impurities nor the recovery of MV-GFP (FIG. 10).

Figure 11:
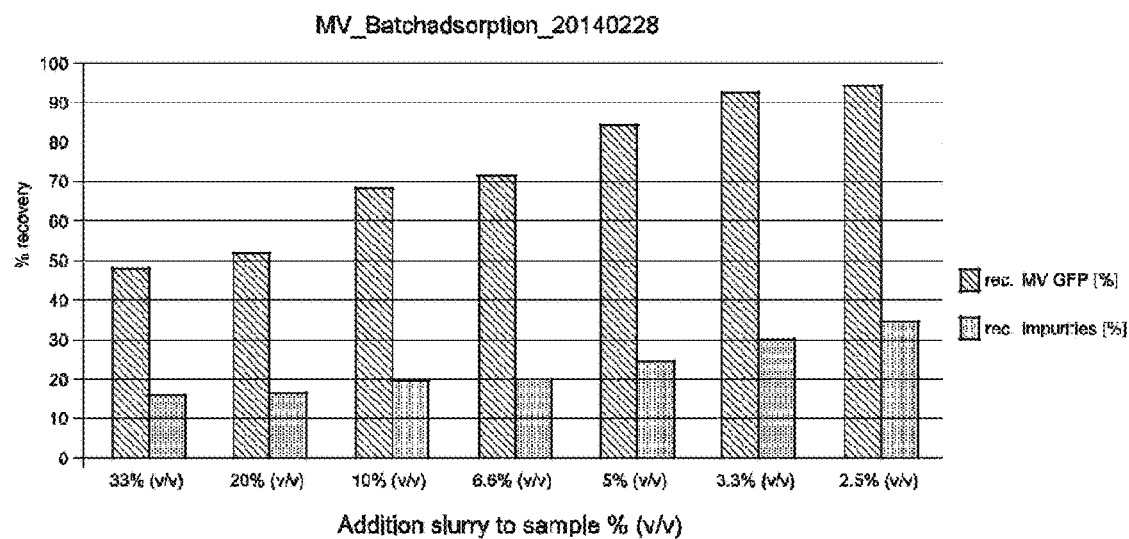
FIG. 11 presents percent recoveries of virus (rec. MV GFP; striped) and impurities (solid gray) as assessed by size exclusion chromatography following batch adsorption using CAPTO® Core 700 resin at various slurry concentrations (33% v/v-2.5% v/v).

The amount of CAPTO® Core 700 slurry added to the viral sample was also optimized. CAPTO® Core 700 slurry (50% in PBS) at concentration from 33% (v/v) to 2.5% (v/v) were tested. Briefly, CAPTO® Core 700 slurry was added to the ultrafiltration/diafiltration MV-GFP harvest and incubated for 2 hours at room temperature. The resins were removed by centrifugation, and the supernatants were analyzed by size-exclusion chromatography. Results indicated that slurry addition >10% (v/v) did not significantly improve the reduction of residual impurities as compared to slurry added 10% (v/v), and further negatively affected MV-GFP recovery (FIG. 11). Slurry additions of less than 10% (v/v) resulted in a small increase in the amount of impurities recovered but improved the amount of virus recovered as compared to the 10% (v/v) sample (FIG. 11). The lowest slurry concentration tested was 2.5% (v/v) and removed approx. 75% of residual impurities compared to the untreated sample (FIG. 11).

Development of Downstream Processing

After optimization of the CAPTO® Core 700 batch adsorption, the method was assessed with samples from MV-GFP downstream process (DSP) development. Samples from several DSP development runs were tested. Briefly, concentrated harvest material was concentrated using the hollow fiber module TFF process described above, and then subjected to various cycles of diafiltration (i.e., 5, 10, 15 and 20 volume changes). An overview of results of all performed experiments is shown in Table 4.

The relative reduction of impurities as compared to material processed without batch adsorption was between 66 to 93%. The purity of the MV preparations ranged from 50 to 76% and was achieved in samples processed with 20 diafiltration cycles (buffer volume exchanges) combined with batch adsorption. The viral yields of material processed with batch adsorption were comparable to the yield of the respective material processed without batch adsorption.

The harvest material was filtered and treated with 50 Units BENZONASE® to digest host cell DNA. The material was concentrated by TFF with a 750 kDa hollow fiber module and subsequently diafiltrated against PBS. Samples were removed from the concentrated material and following 5, 10, 15 and 20 volumes exchanges. CAPTO® Core 700 slurry was added at a concentration of 10% (v/v) to samples of each stage. The samples were incubated for 2 hours at room temperature. The resin was removed by centrifugation, and the supernatants were analyzed by size-exclusion chromatography and SDS-PAGE gel electrophoresis.

Figure 12:
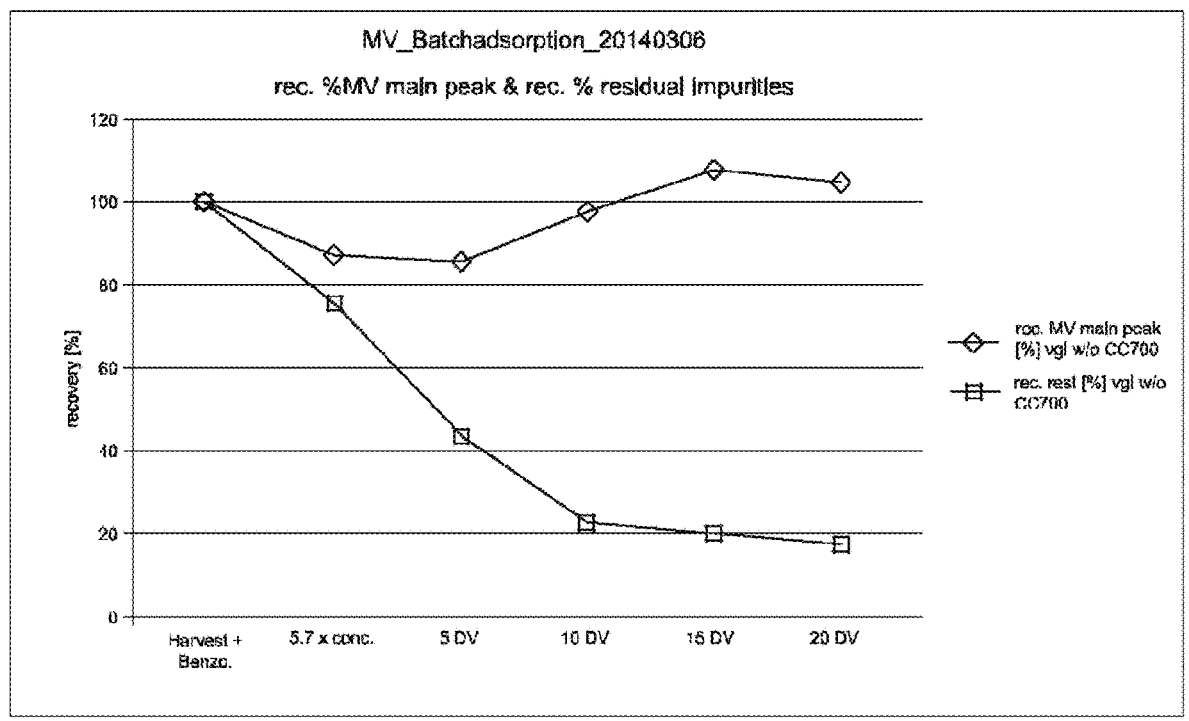
FIG. 12 shows percent recoveries of virus (rec. MV main peak; diamonds) and residual impurities (rec. rest; squares) in batch absorption samples as assessed by size exclusion chromatography.
Figure 13:
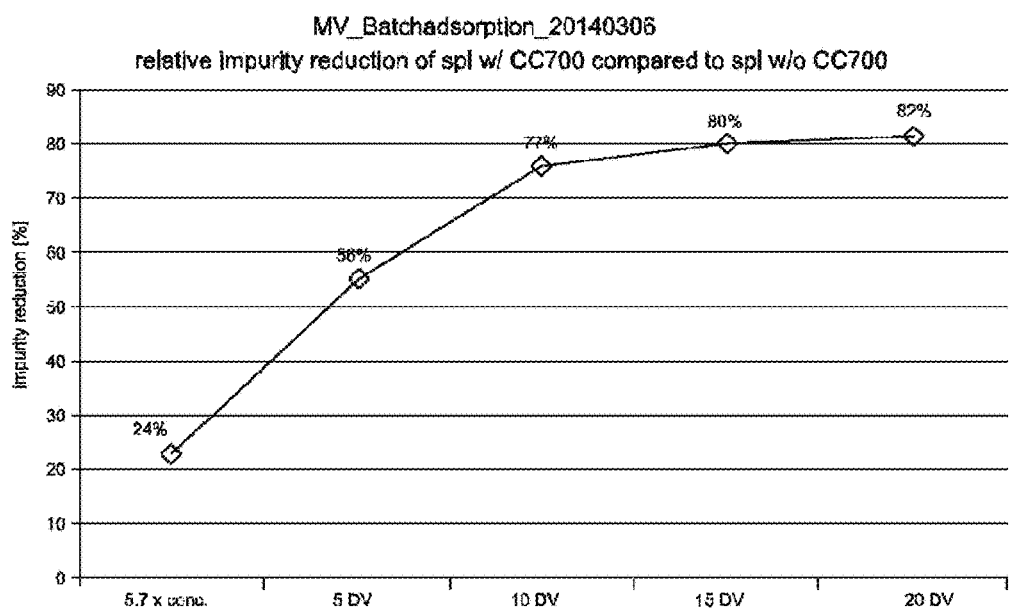
FIG. 13 shows the relative reduction in residual impurities of samples processed with batch adsorption relative to samples that were not batch adsorbed.

The recoveries of MV-GFP and residual impurities in samples subjected to batch adsorption and samples that were not subjected to batch adsorption as presented in FIG. 12. The relative reduction of residual impurities in samples with batch adsorption relative to sampled without batch adsorption is shown in FIG. 13. While the relative MV-GFP recovery remained stable across the samples, the residual impurities were significantly reduced by batch adsorption using CAPTO® Core 700 samples. An 82% reduction in recovered impurities was achieved when the samples were processed with 20 diafiltration volume changes (20 DV) and batch adsorption using CAPTO® Core 700 resin as compared to samples processed with 20 DV but no batch adsorption.

Figure 14:
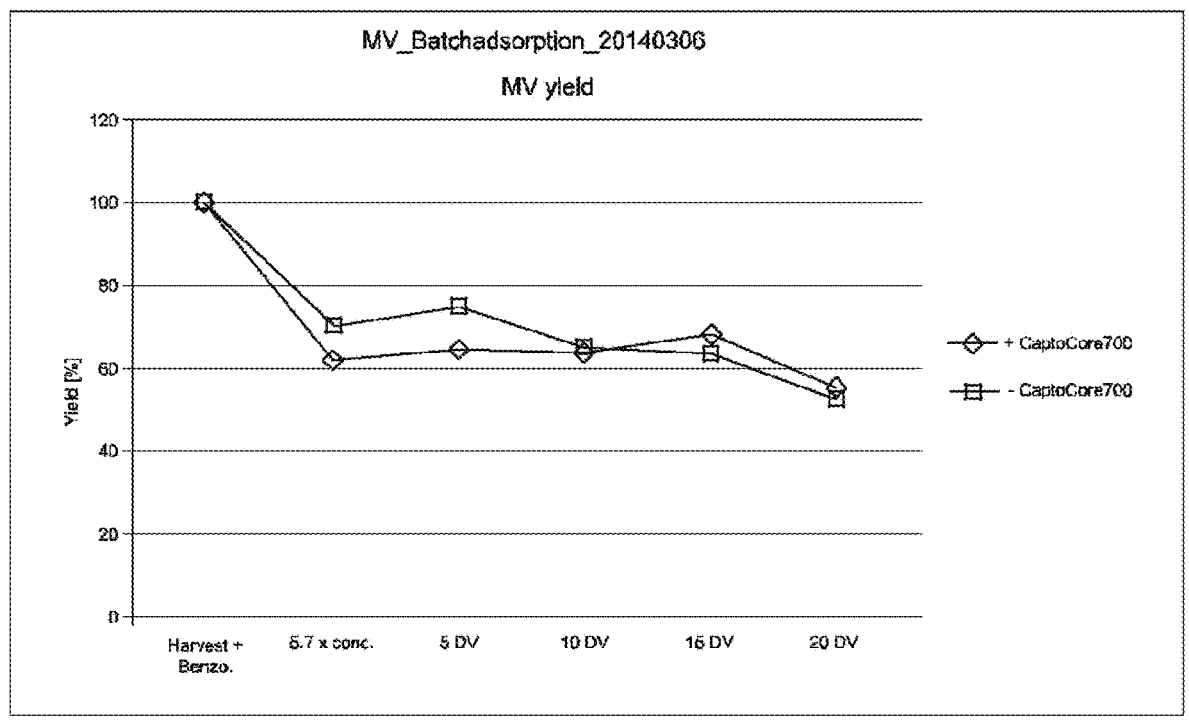
FIG. 14 presents the overall yield of MV-GFP in samples processed with CAPTO® Core 700 batch adsorption (diamonds) or without batch adsorption (squares).

The overall yields of MV-GFP recovered from samples processed with and without batch adsorption were calculated with data from size exclusion chromatography (FIG. 14). MV-GFP yield after 20 diafiltration cycles was 51% in samples processed without batch adsorption and 54% for the samples processed with batch adsorption.

Figure 15:
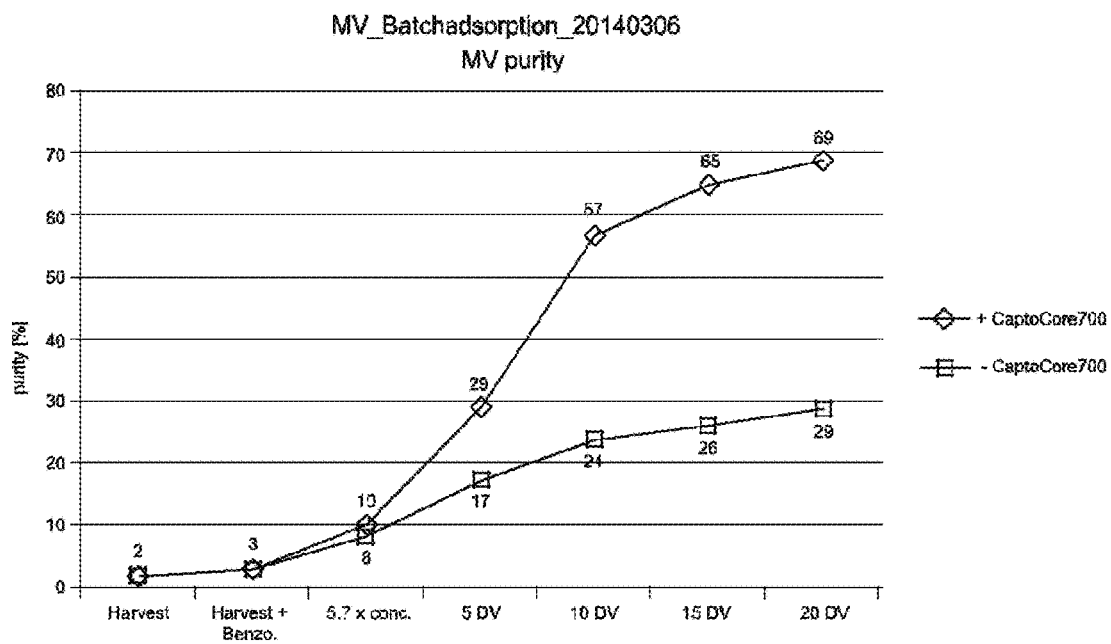
FIG. 15 shows the purity of MV-GFP in samples processed with CAPTO® Core 700 batch adsorption (diamonds) or without batch adsorption (squares) at various stages during the purification process as assessed by size exclusion chromatography.
Figure 16:
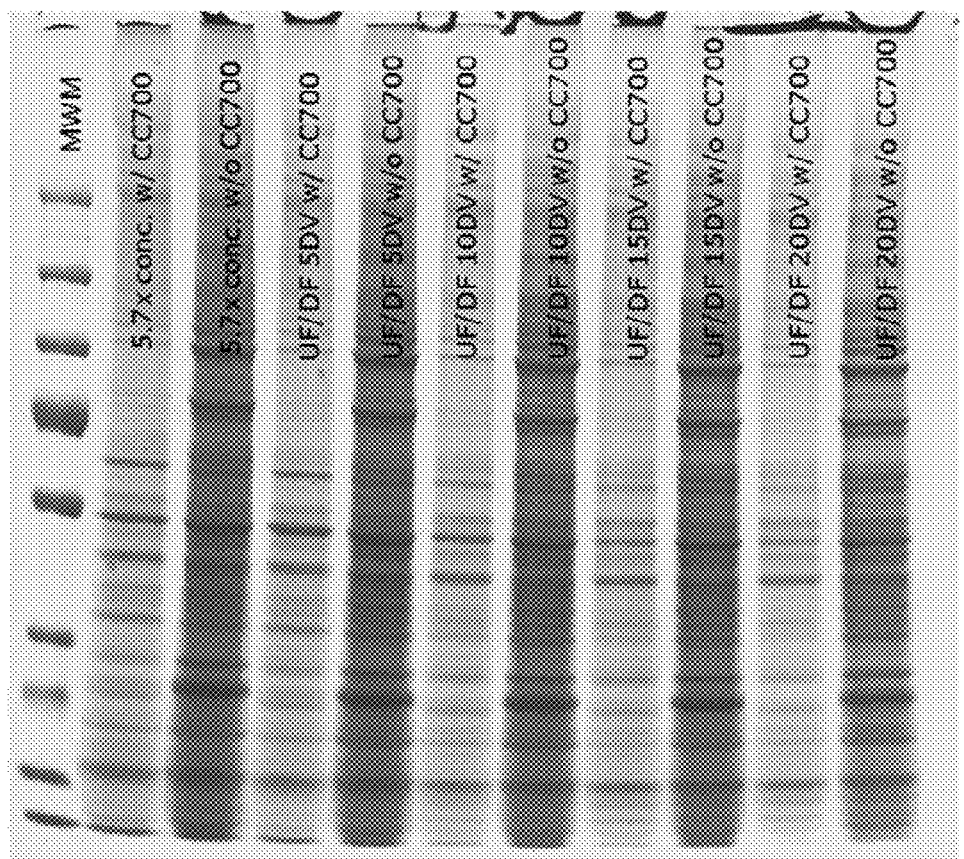
FIG. 16 shows the purity of MV-GFP in samples processed with CAPTO® Core 700 batch adsorption ("w/ CC700") or without batch adsorption ("w/o CC700") at various stages during the purification process as assessed by SDS-PAGE gel.

Purity of MV-GFP material after each process stage was assessed quantitatively using size exclusion chromatography and qualitatively using SDS-PAGE electrophoresis. Purity of the MV-GFP material was significantly improved after batch adsorption (FIG. 15 and FIG. 16). While the maximum purity achieved without batch adsorption was 29% with the 20 DV sample, a comparable purity was already achieved after only 5 diafiltration volume exchanges (5 DV) combined with batch adsorption. This presents a significant reduction in processing time. The highest level of purity (69%) was achieved with the 20 DV sample combined with batch adsorption.

Figure 17:
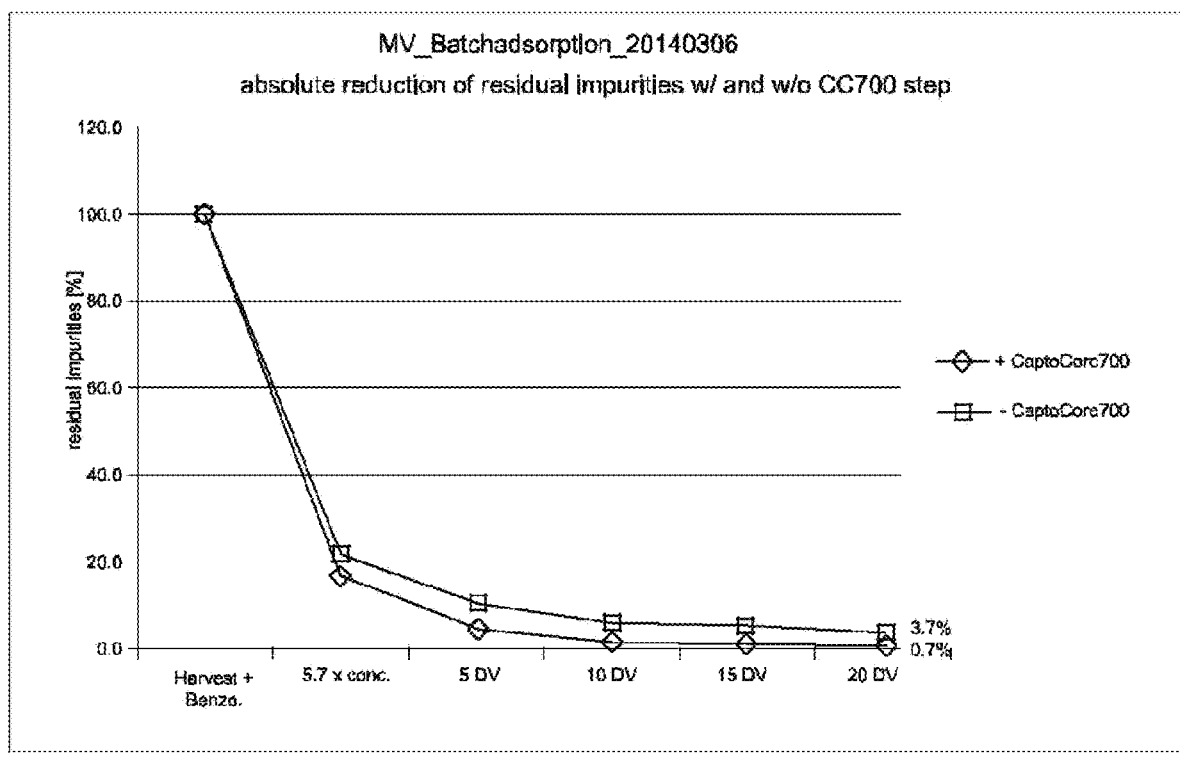
FIG. 17 shows the percent residual impurities in samples processed with CAPTO® Core 700 batch adsorption (diamonds) or without batch adsorption (squares) at various stages during the purification process as assessed by size exclusion chromatography.

The reduction of residual impurities in samples processed with and without batch adsorption as compared to a concentrated harvest sample is shown in FIG. 17. Without batch adsorption, residual impurities were reduced 96% or log 1.4. Using CAPTO® Core 700 batch adsorption, residual impurities were reduced >99% or log 2.2.

In conclusion, batch adsorption using CAPTO® Core 700 resin enabled a significant reduction of residual impurities without a negative impact on virus yield. Batch adsorption with CAPTO® Core 700 resin resulted in a level of virus purity that was not attainable using diafiltration only. Purity levels after 20 diafiltration cycles without batch adsorption were achieved with only 5 diafiltration cycles combined with batch adsorption.

TABLE 4

Overview of MV batch adsorption experiments

| Experiment | MV material | DV | Impurity reduction comp. to spl. w/o CC700 (%) | MV Purity (%) | | MV Yield (%) | |
| --- | --- | --- | --- | --- | --- | --- | --- |
| | | | | w/CC700 | w/o CC700 | w/CC700 | w/o CC700 |
| MV Batchadsorption 20140306 | MV Harvest RG25, pooled Filtertest 20140207 samples, digestion w/50 U Benzonase o/n, RT°, 5.7 x conc | 5 10 15 20 | 56 77 80 82 | 29 57 65 69 | 17 24 26 29 | 64 63 67 54 | 74 64 62 51 |
| MV Batchadsorption 20140314 | MV Harvest RG25, pooled Filtertest 20140207 samples, digestion w/50 U Benzonase o/n, RT°, 5.7 x conc | 5 10 15 20 | n.a. 68 71 66 | 17 38 47 50 | n.a. 16 20 22 | 19 25 29 24 | n.a. 25 28 24 |
| MV Batchadsorption 20140320 | MV Harvest RG25, pooled Filtertest 20140206 A-C samples, 5.6 x conc | 5 10 15 20 | 45 62 71 69 | 30 55 72 76 | 18 30 41 48 | 105 86 72 66 | 99 81 67 64 |
| MV Batchadsorption 20140327 | MV Harvest RG25, digestion w/50 U Benzonase o/n, RT°, 10 x conc | 5 10 15 20 | 32 63 70 93 | 13 37 50 61 | 9 18 22 25 | 45 30 28 26 | 46 31 27 22 |
| MV Batchadsorption 20140424 | MV Harvest RG25, digestion w/5 U Benzonase o/n, RT°, 10 x conc | 5 10 | 43 59 | 17 29 | 10 16 | 202 193 | 194 206 |

What is claimed is:

1. A process of purification of virus particles wherein the virus particles belong to the Coronaviridae virus family, comprising the steps of:
   (a) providing a liquid medium comprising said virus particles, wherein the virus particles are greater than or equal to about 100 nm in diameter;
   (b) contacting the virus particles with a solid-phase matrix comprising a ligand-activated core and an inactive shell comprising pores having a molecular weight cut off that excludes the virus particles from entering the ligand-activated core, and wherein a molecule smaller than the molecular weight cut off of the pores can enter the ligand-activated core; and
   (c) separating the solid-phase matrix from the virus particles to produce a final virus preparation;
   wherein the solid-phase matrix is added to the liquid medium comprising the virus particles at a final concentration between 2.5% (v/v) and 30% (v/v); and
   wherein each step of the process is performed aseptically.

2. The process of claim 1, wherein the liquid medium comprising the virus particles is subjected to one or more pre-purification step(s) prior to step (b).

3. The process of claim 1, wherein the virus particles are about 200 nm, 300 nm, 400 nm, 500 nm or more in diameter.

4. The process of claim 1, wherein the molecule entering the core of the solid-phase matrix has a molecular weight less than 700 kDa.

5. The process of claim 1, wherein the ligand of the ligand-activated core of the solid-phase matrix is octylamine.

6. The process of claim 1, wherein the relative reduction of impurity of the final virus preparation relative to the liquid medium comprising the plurality of the viruses or virus particles is in a range from 60 to 95%.

7. The process of claim 2, wherein the pre-purification step comprises
  (i) digesting host cell genomic DNA in the liquid medium comprising the plurality of the viruses or virus particles by enzymatic treatment; and/or
  (ii) ultra/diafiltration of the liquid medium comprising the plurality of the viruses or virus particles using a hollow fiber membrane having a pore size equal or greater than 750 kDa.

8. The process of claim 1, wherein the process is followed by one or more aseptic filtration step(s).

9. The process of claim 1, wherein the residual impurity of the final virus preparation is less than 1%.

10. The process of claim 1, wherein the liquid medium comprising said virus particles is produced in a cell culture by propagating the virus in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, an MDSK cell line, a chicken embryonic fibroblast cell line, a duck cell line, and a diploid avian cell line.

11. The process of claim 10, wherein said cell line is EB66 cell line.

12. A method for manufacturing a composition for immunization against a viral infection caused by a virus of the Coronaviridae family comprising the steps of:
  (a) providing a liquid medium comprising virus particles belonging to the Coronaviridae family, wherein the virus particles are greater than or equal to about 100 nm in diameter;
  (b) contacting the virus particles with a solid-phase matrix comprising a ligand-activated core and an inactive shell comprising pores having a molecular weight cut off that excludes the virus particles from entering the ligand-activated core, and wherein a molecule smaller than the molecular weight cut off of the pores can enter the ligand-activated core;
  (c) separating the solid-phase matrix from the virus particles to produce a final virus preparation; and
  (d) obtaining a sterile composition comprising the highly purified virus preparation,
  wherein the solid-phase matrix is added to the liquid medium comprising the virus particles at a final concentration between 2.5% (v/v) and 30% (v/v); and wherein each step of the process is performed aseptically.

* * * * *